(12) United States Patent
Lee et al.

(10) Patent No.: US 10,595,757 B2
(45) Date of Patent: Mar. 24, 2020

(54) APPARATUS AND METHOD FOR MEASURING BIOLOGICAL COMPONENT

(71) Applicant: SAMSUNG ELECTRONICS CO., LTD., Suwon-si (KR)

(72) Inventors: Joon Hyung Lee, Seononam-si (KR); Jung Yong Nam, Hwaseong-si (KR); Ki Young Chang, Yongin-si (KR); Kak Namkoong, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 289 days.

(21) Appl. No.: 15/581,262

(22) Filed: Apr. 28, 2017

(65) Prior Publication Data

US 2018/0132766 A1  May 17, 2018

(30) Foreign Application Priority Data

Nov. 15, 2016 (KR) ........................ 10-2016-0152204

(51) Int. Cl.
*A61B 5/1455* (2006.01)
*G01N 21/49* (2006.01)
(Continued)

(52) U.S. Cl.
CPC .......... *A61B 5/1455* (2013.01); *A61B 5/0075* (2013.01); *A61B 5/443* (2013.01);
(Continued)

(58) Field of Classification Search
CPC ... A61B 5/1455; A61B 5/0075; A61B 5/4872; A61B 5/443; A61B 2562/043;
(Continued)

(56) References Cited

U.S. PATENT DOCUMENTS

| 4,623,248 | A | * | 11/1986 | Sperinde | ............... | A61B 5/1459 |
| | | | | | | 356/41 |
| 5,795,305 | A | | 8/1998 | Cho et al. | | |
| 6,752,760 | B2 | | 6/2004 | Kouou | | |
| 7,860,547 | B2 | | 12/2010 | Kondoh et al. | | |
| 8,095,211 | B2 | | 1/2012 | Tamura et al. | | |
| 8,102,525 | B2 | | 1/2012 | Guo et al. | | |

(Continued)

FOREIGN PATENT DOCUMENTS

| EP | 1595498 A1 | 11/2005 |
| JP | 2004-226277 A | 8/2004 |

(Continued)

OTHER PUBLICATIONS

Ahn, et al., "Blood Glucose Measurement Principles of Non-invasive Blood Glucose Meter: Focused on the Detection Methods of Blood Glucose", 2012, Journal of Biomedical Engineering Research, vol. 33, pp. 114-127.

*Primary Examiner* — Eric F Winakur
*Assistant Examiner* — Abid A Mustansir
(74) *Attorney, Agent, or Firm* — Sughrue Mion, PLLC

(57) ABSTRACT

An apparatus for measuring a biological component includes: light sources configured to emit light that irradiates a target object; one or more detectors configured to receive light from the target object that is irradiated by the light emitted by the light sources and to detect light signals corresponding to the light received from the target object; and a processor configured to determine an optimal light source for measuring a biological component, from among the light sources, based on the light signals detected by the one or more detectors and to measure a biological component of the target object using the optimal light source.

14 Claims, 10 Drawing Sheets

(51) Int. Cl.
*G01N 21/47* (2006.01)
*A61B 5/00* (2006.01)
*G01J 3/50* (2006.01)
*A61B 5/145* (2006.01)

(52) U.S. Cl.
CPC ............ *A61B 5/4872* (2013.01); *G01J 3/505* (2013.01); *G01N 21/47* (2013.01); *G01N 21/474* (2013.01); *G01N 21/49* (2013.01); *A61B 5/14532* (2013.01); *A61B 5/14546* (2013.01); *A61B 2562/043* (2013.01); *G01N 2021/4783* (2013.01); *G01N 2201/12* (2013.01)

(58) Field of Classification Search
CPC ............ A61B 5/14532; A61B 5/14546; G01N 21/474; G01N 21/49; G01N 21/47; G01N 2021/4783; G01N 2201/12; G01J 3/505
See application file for complete search history.

(56) References Cited

U.S. PATENT DOCUMENTS

| | | | |
|---|---|---|---|
| 2004/0162493 A1* | 8/2004 | Mills ................. | A61B 5/02028 600/481 |
| 2011/0137199 A1 | 6/2011 | Karo et al. | |
| 2012/0253153 A1* | 10/2012 | Trumble ............ | A61B 5/14551 600/324 |
| 2014/0236019 A1 | 8/2014 | Rahum | |
| 2016/0228582 A1 | 8/2016 | Dietrich et al. | |
| 2017/0360316 A1* | 12/2017 | Gu ..................... | A61B 5/02433 |

FOREIGN PATENT DOCUMENTS

| | | |
|---|---|---|
| JP | 2012-68263 A | 4/2012 |
| KR | 10-2013-0062858 A | 6/2013 |
| KR | 10-1494902 B1 | 2/2015 |
| WO | 95/15711 A1 | 6/1995 |
| WO | 01/70330 A2 | 9/2001 |
| WO | 2015/059636 A1 | 4/2015 |

* cited by examiner

APPARATUS AND METHOD FOR MEASURING BIOLOGICAL COMPONENT

CROSS-REFERENCE TO RELATED APPLICATION(S)

This application claims priority from Korean Patent Application No. 10-2016-0152204, filed on Nov. 15, 2016 in the Korean Intellectual Property Office, the entire disclosure of which is incorporated herein by reference in its entirety.

BACKGROUND

1. Field

Apparatuses and methods consistent with exemplary embodiments relate to non-invasively measuring a biological component, and more particularly, to emitting light for measuring a biological component, such as neutral fat, and measuring a biological component using a detected light signal.

2. Description of Related Art

A level of neutral fat may be elevated by causes, such as obesity, lack of exercise, and smoking. A high level of neutral fat may be associated with metabolic syndrome and act as a risk factor for arteriosclerosis, and hence management of the concentration of neutral fat is needed. Among methods of measuring an in vivo level of neutral fat, an invasive method may allow for measuring an accurate concentration of neutral fat, but it is difficult to manage a person's health through regular measurements because this method incurs psychological and physical pain.

Accordingly, methods of non-invasively measuring a biological component have been attempted. As one of such methods, a method of measuring a change of neutral fat in a blood vessel by emitting light to the skin of a target object and using a signal reflected from the skin is being studied.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an exemplary embodiment, there is provided apparatus for measuring a biological component, the apparatus including: light sources configured to emit light that irradiates a target object; one or more detectors configured to receive light from the target object that is irradiated by the light emitted by the light sources and to detect light signals corresponding to the light received from the target object; and a processor configured to determine an optimal light source for measuring a biological component, from among the light sources, based on the light signals detected by the one or more detectors and to measure a biological component of the target object using the optimal light source.

The processor may include a signal-to-noise ratio determiner configured to determine signal-to-noise ratios of light signals detected by the one or more detectors.

The processor may further include a light source determiner configured to select at least one detector, from among the one or more detectors, based on the signal-to-noise ratios and to determine the optimal light source based on the signal-to-noise ratios of light signals detected by the at least on detector that is selected.

The processor may be further configured to determine an average of signal-to-noise ratios of the light signals detected by the at least one detector and determines the optimal light source based on the average.

The processor may further include a detector determiner configured to determine an optimal detector for measuring the biological component, from among the one or more detectors, based on the signal-to-noise ratios.

The detector determiner may be further configured to determine the optimal detector according to signal-to-noise ratios of light signals corresponding to the optimal light source.

The processor may further include a component measurer configured to control the optimal light source and the optimal detector and to measure the biological component on a light signal corresponding to the optimal light source which is detected by the optimal detector.

The component measurer may be further configured to determine a scattered coefficient based on a backscattered light intensity of a light signal detected by the optimal detector and to measure the biological component of the target object based on the scattered coefficient.

The light sources may be further configured emit light of different wavelength bands and the one or more detectors are arranged in one of a rectangular array and a radial array.

The biological component may include at least one of neural fat, cholesterol, proteins, blood sugar, and uric acid.

The apparatus may further include: a communicator configured to be communicably connected with an external device and to transmit a biological component measurement result to the external device in response to a control signal from the processor; and an output unit configured to output the biological component measurement result.

The apparatus may further include a sensor configured to sense whether a measurement position of the target object is changed, and the processor may be further configured to repeat determination of the optimal light source in response to the sensor detecting that the measurement position of the target object is changed.

According to an aspect of another exemplary embodiment, there is provided a method of measuring a biological component, the method including: receiving, at one or more detectors, light from a target object that is irradiated with light by light sources; detecting, at the one or more detectors, light signals corresponding to the light from the target object; determining an optimal light source for measuring a biological component of the target object, from among the light sources, based on the light signals detected by the one or more detectors; and measuring a biological component using the optimal light source.

The method may further include determining signal-to-noise ratios of the light signals detected by the one or more detectors.

The determining the optimal light source may include selecting at least one detector among the one or more detectors based on the signal-to-noise ratios, and determining the optimal light source based on the signal-to-noise ratios of the light signals detected by the at least one detector that is selected.

The determining the optimal light source may include determining an average of signal-to-noise ratios of the light signals detected by the at least one detector that is selected, and determining the optimal light source based on the average.

The method may further include determining an optimal detector for measuring a biological component, from among the one or more detectors, based on the signal-to-noise ratios.

The determining the optimal detector may include determining the optimal detector according to signal-to-noise ratios of light signals corresponding to optimal light source.

The measuring the biological component may include controlling the optimal light source and the optimal detector, and measuring the biological component based on a light signal corresponding to the optimal light source which is detected by the optimal detector.

The determining the optimal light source may include determining a scattered coefficient based on a backscattered light intensity of a light signal detected by the optimal detector, and measuring the biological component based on the scattered coefficient.

BRIEF DESCRIPTION OF THE DRAWINGS

The above and/or other aspects will become apparent and more readily appreciated from the following description of exemplary embodiments, taken in conjunction with the accompanying drawings in which.

DETAILED DESCRIPTION

Figure 1:
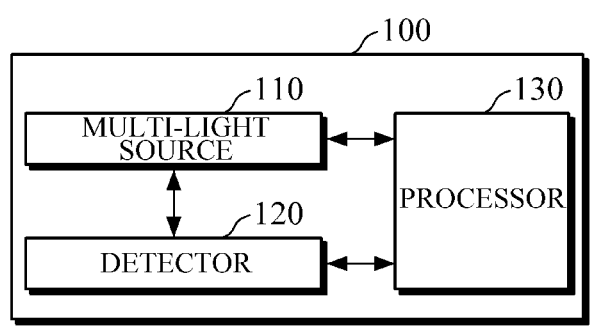
FIG. 1 is a block diagram illustrating an apparatus for measuring a biological component according to an exemplary embodiment.

The following detailed description is provided to assist the reader in gaining a comprehensive understanding of the methods, apparatuses and/or systems described herein. Various changes, modifications, and equivalents of the systems, apparatuses and/or methods described herein will suggest themselves to those of ordinary skill in the art. In the following description, a detailed description of known functions and configurations incorporated herein may be omitted when it may obscure the subject matter with unnecessary detail.

Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises," "comprising," "includes," and "including," will be understood to imply the inclusion of stated elements but not the exclusion of any other elements. Terms such as " . . . unit" and "module" denote components that perform at least one function or operation, and may be implemented by hardware, software, or a combination of hardware and software.

Hereinafter, apparatuses and methods for measuring a biological component will be described with reference to the accompanying drawings.

Figure 2A:
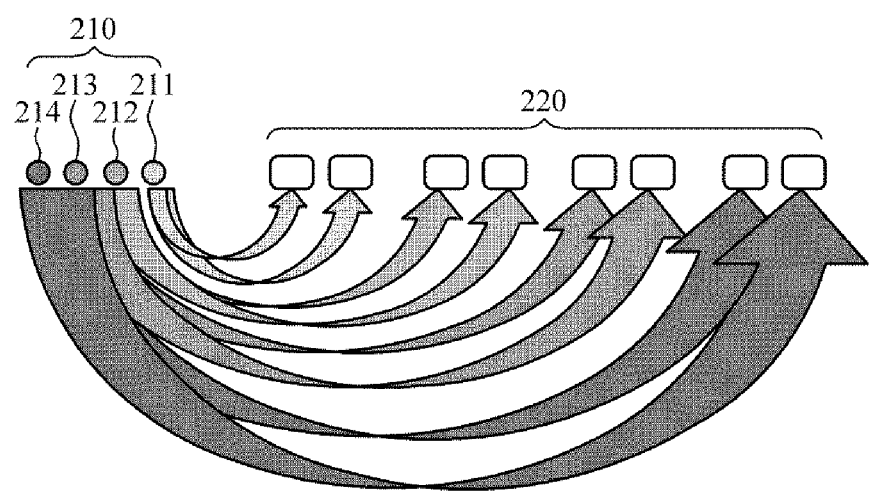
FIGS. 2A and 2B are diagrams for describing biological component measurement performed by the apparatus for measuring a biological component.
Figure 2B:
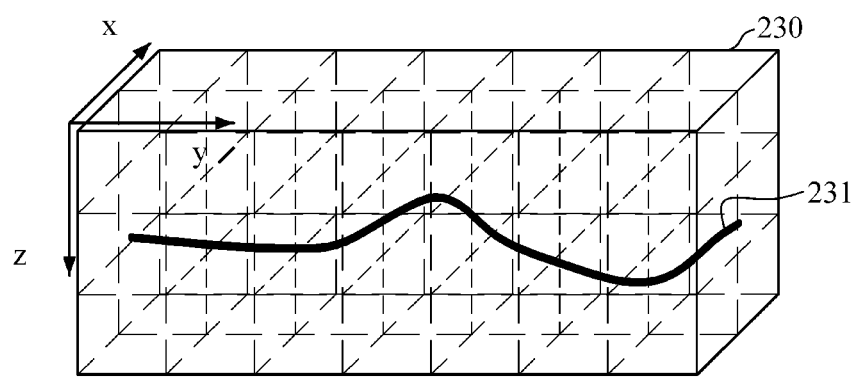

FIG. 1 is a block diagram illustrating an apparatus for measuring a biological component according to an exemplary embodiment. FIGS. 2A and 2B are diagrams for describing biological component measurement performed by the apparatus for measuring a biological component.

Referring to FIG. 1, the apparatus 100 for measuring a biological component includes a multi-light source 110, a detector 120, and a processor 130. The processor 130 may be configured with one or more processors, memories, and a combination thereof.

The multi-light source 110 may emit light to a target object. For example, the multi-light source 110 may be multiple light sources including one or more light sources which emit light of a specific visible wavelength band, a near infrared ray (NIR) band, or a mid-infrared ray (MIR) band. In addition, the multi-light source 110 may include one or more light sources consisting of independent modules, and each light source may be set to emit light of a different wavelength band. However, embodiments are not limited thereto, and the multi-light source 110 may be physically configured as a single module, or may be set to repetitively and sequentially emit light of multiple wavelength bands.

The detector 120 may receive the light emitted from the multi-light source 110. In this case, the detector 120 may include a photodiode, a photo transistor (PTr), or a charge-coupled device (CCD), but is not limited thereto. For example, the detector 120 may detect a light signal from light reflected from the skin of the target object which is irradiated by the multi-light source, absorption light, and/or light scattered by a biological component. In addition, one or more detectors 120 may be provided, and may be implemented as an array of a predetermined structure spaced apart from the multi-light source 110 at a specific distance. Hereinafter, the term "light signal" may refer to a signal obtained by one or more detectors 120 which detect light scattered by a biological component which is irradiated by the multi-light source 110.

The processor 130 may determine an optimal light source for measuring a biological component based on each light signal detected by each of the one or more detectors. For example, the optimal light source for measuring a biological component may vary depending on the positions of the multi-light source 110 and the detector 120, and the optimal light source may refer to a light source at a specific location among one or more light sources included in the multi-light source 110. However, embodiments are not limited to the above description, and when the multi-light source 110 includes one or more light sources, each of which is set to emit light of a specific wavelength band, the optimal light source may refer to a light source which emits light of a particular wavelength band.

For example, FIG. 2A is a diagram illustrating an example in which a multi-light source is set to emit light of different wavelength bands. Referring to FIGS. 1 and 2A, the multi-light source 110 may be a multi-light source 210 including a blue light source 211 (e.g., a wavelength band of 450 nm), a green light source 212 (e.g., a wavelength band of 550 nm), a red light source 213 (e.g., a wavelength band of 700 nm), and an infrared light source 214 (e.g., a wavelength band of 1100 nm). In this case, light of a longer wavelength penetrates the skin deeper, and when considering the optical path according to a wavelength, light signals caused by scattering which are detected by one or more detectors 220 may be measured differently for each detector 210 according to a distance between the skin and the blood vessel (e.g., a depth of the blood vessel). In one example, the processor 130 may calculate a signal-to-noise ratio (SNR) of each of the light signals detected by one or more detectors 120 and select a light source which emits light of a wavelength band with the highest SNR as the optimal light source. FIG. 2A illustrates the multi-light source 210 which emit light of different wavelength bands, but this is merely an example for convenience of description and thus the multi-light source is not limited thereto. For example, the multi-light source 210 may be set to emit light of the same wavelength band, and the processor 130 may calculate an SNR of each light signal detected by each of one or more detectors, and select a light source at a position at which the highest SNR is calculated as the optimal light source. At this time, the light sources included in the multi-light source 210 may be sequentially flashed to specify the positions thereof.

In addition. FIG. 2B illustrates a blood vessel 231 located below the skin 230 of the target object. Referring to FIGS. 1 and 2B, a distance (e.g., z-axis) between the skin 230 of the target object and the blood vessel 231 may vary depending on a position at which a biological component of the target object is measured. The apparatus 100 for measuring a biological component uses the multi-light source 110 and one or more detectors 120, thereby accurately measuring a biological component by determining an optimal light source and/or an optimal detector using characteristics of detected light signals even when a depth of the blood vessel 231 varies according to the position at which the biological component is measured.

The processor 130 may measure the biological component using the determined optimal light source. In this case, the biological component may include at least one of neural fat, cholesterol, proteins, blood sugar, and uric acid, but is not limited thereto. For convenience of description, hereinafter, the description will focus on exemplary embodiments in which the apparatus measures the concentration of neutral fat, but embodiments are not limited thereto.

The processor 130 may measure the concentration of neutral fat based on a backscattered intensity detected from the light of the determined optimal light source using Equation 1 below. Equation 1 assumes that the concentration of neutral fat is measured using an optimal light source having a specific wavelength and light signals detected by two optimal detectors (e.g., a first detector and a second detector) for the optimal light source.

$$\mu_s' = \frac{1}{3\mu_a}\left\{\frac{1}{\rho_2-\rho_1}\ln\frac{\rho_1^2 R_1(\rho_1)}{\rho_2^2 R_2(\rho_2)}\right\} \quad (1)$$

In Equation 1, $\mu_s'$ denotes a reduced scattering coefficient, $\mu_a$ denotes an absorption coefficient, $\rho_1$ denotes a distance from the determined optimal light source to the first detector, $\rho_2$ denotes a distance from the determined optimal light source to the second detector, $R_1$ denotes a backscattered intensity at the first detector, and $R_2$ denotes a backscattered intensity at the second detector. For example, the processor 130 may select at least two detectors and calculate a reduced scattering coefficient which may be defined as a ratio of backscattered intensities detected at the two selected detectors so as to measure the concentration of neutral fat of the target object. For example, the processor 130 may calculate a reduced scattering coefficient in a reference state (e.g., fasting state) in which a biological component of the target object does not change, calculate a reduced scattering coefficient after a predetermined amount of time has elapsed since consumption of food containing fat, and compute an amount of change in the reduced scattering coefficient, thereby calculating the concentration of neutral fat. Here, the reference state may be set differently according to the age, sex, and skin condition of a user, and the type of biological component to be measured.

Figure 3:
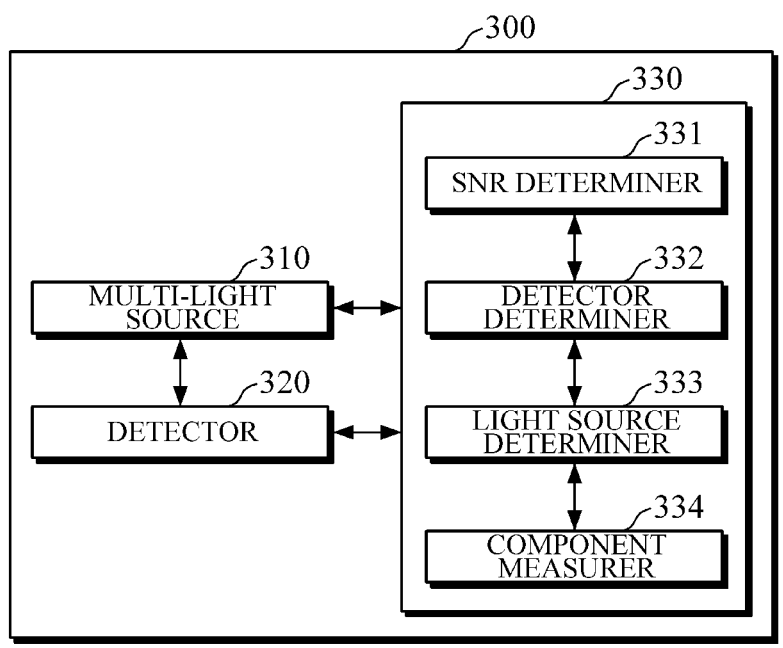
FIG. 3 is a block diagram illustrating an apparatus for measuring a biological component according to another exemplary embodiment.
Figure 4A:
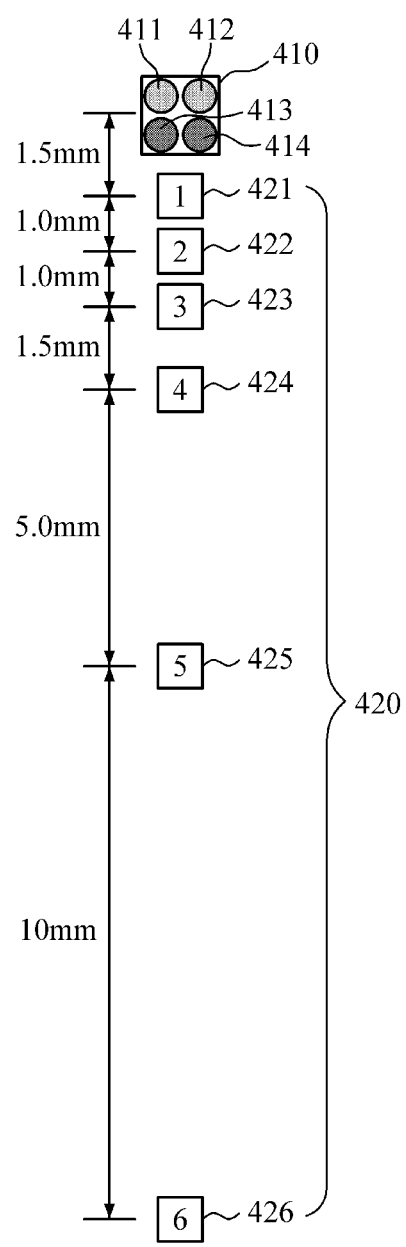
FIG. 4A is a diagram for describing determination of an optimal light source and an optimal detector of the apparatus according to one exemplary embodiment.
Figure 4B:
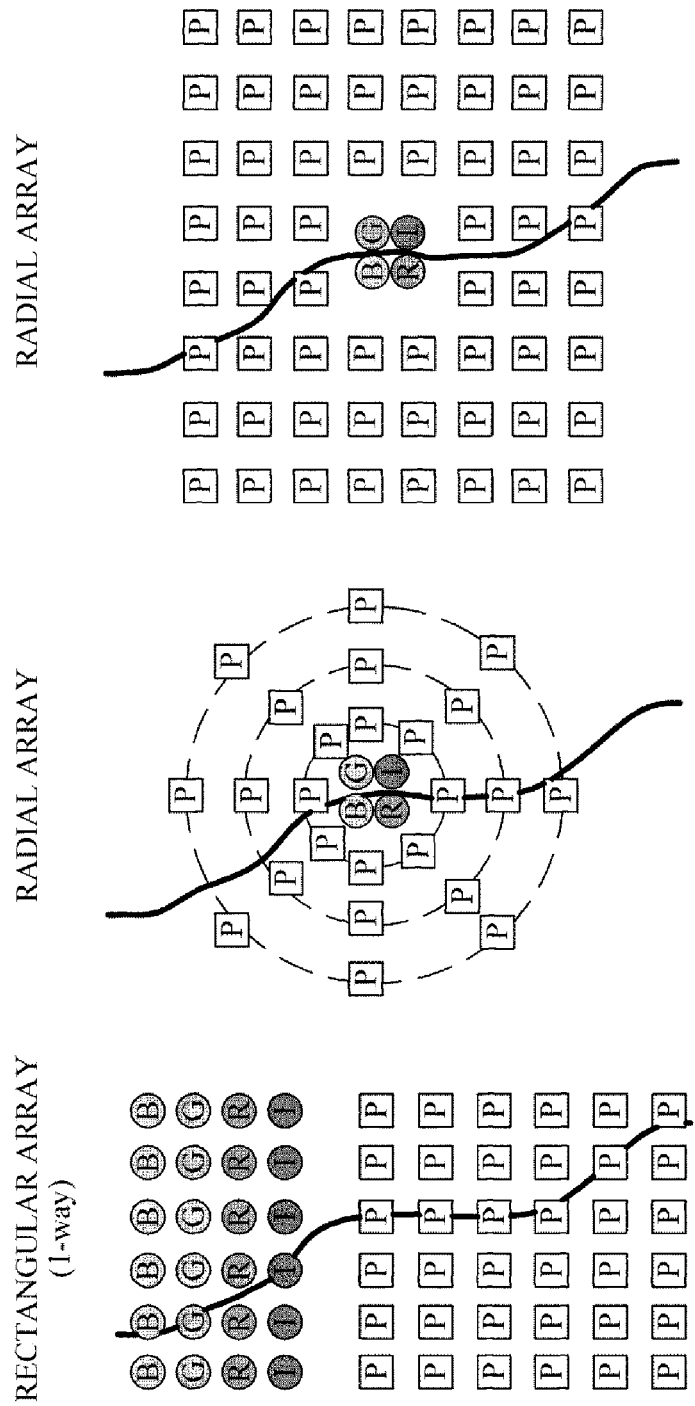
FIG. 4B is a diagram for describing arrays of multiple light sources and detectors of the apparatus for measuring a biological component.

FIG. 3 is a block diagram illustrating an apparatus for measuring a biological component according to another exemplary embodiment. FIG. 4A is a diagram for describing determination of an optimal light source and an optimal detector of the apparatus according to an exemplary embodiment, and FIG. 4B is a diagram for describing arrays of multiple light sources and detectors of the apparatus for measuring a biological component.

Referring to FIG. 3, the apparatus 300 for measuring a biological component includes a multi-light source 310, a detector 320, and a processor 330, and the processor 330 includes an SNR determiner 331, a detector determiner 332, a light source determiner 333 and a component measurer 334. In this case, the multi-light source 310 and the detector 320 are configured to be basically the same as the multi-light source 110 and the detector 120 of FIG. 1, and hereinafter, a description will be given focusing on a configuration which is not redundant.

The SNR determiner 331 may calculate an SNR of each light signal detected by one or more detectors 320 for each light source of the multi-light source 310. Hereinafter, an example in which the SNR determiner 331 calculates an SNR of each light source detected by one or more detectors 320 for each light source of the multi-light source 310 will be described with reference to FIGS. 3 and 4A.

The multi-light source 410 may include one or more light sources 411, 412, 413, and 414. In this case, one or more light sources 411 to 414 included in the multi-light source are disposed at different locations and include green light sources 411 and 412 and red light sources 413 and 414. In addition, a detector 420 may include one or more detectors 421, 422, 423, 424, 425, and 426, and the multiple detectors 421 to 426 may be spaced apart from the respective light sources of the multi-light source 410 at specific distances.

For example, the SNR determiner 331 may calculate an SNR for each light source 411 to 414 based on the light signal detected by each of the detectors 421 to 426. For example, the SNR determiner 331 may calculate an SNR for each of the light sources 411 to 414 using a light signal detected by the detector 421 and calculate an SNR for each of the light sources 411 to 414 using a light signal detected by the detector 422. In this manner, the SNR determiner 331 may calculate the SNR for each of the light sources 411 to 414 using each light signal detected by each of the detectors 421 to 426.

The detector determiner 332 may determine an optimal detector for measuring a biological component based on the calculated SNRs. The optimal detector for measuring a biological component emits light and may vary according to a position at which the biological component is measured. The detector determiner 332 may determine the optimal detector based on the calculated SNRs, regardless of change in measurement position.

For example, referring to FIGS. 3 and 4A, the detector determiner 332 may determine the optimal detector for measuring a biological component according to the values of SNRs calculated by each of the detectors 421 to 426. For example, when considering a traveling path of the light wavelength, in the case of the back of a hand where the blood vessel is located close to the skin, SNRs of light signals detected by detectors (e.g., 421 to 424) located close to the multi-light source 310 may be calculated to be high. In this case, the detector determiner 332 may select the detectors (e.g., 421 and 422) having the highest SNR as the optimal detectors.

In another example, referring back to FIGS. 3 and 4A, when considering a traveling path of the light wavelength, in the case of the wrist where the blood vessel is located further away from the skin, SNRs of light signals detected by the detectors (e.g., 425 and 426) located farther from the multi-light source 310 may have low values. In this case, the detector determiner 332 may select the detectors (e.g., 425 and 426) having the highest SNR as the optimal detectors for measuring a biological component.

In still another example, the detector determiner 332 may calculate an SNR of a light signal detected from the light emitted from each of the light sources 411 to 414 of the multi-light source 310, sum up the SNRs at each of the detectors 421 to 426, and calculate an average of the SNRs at each of the detectors 421 to 426, thereby selecting at least some detectors as optimal detectors for measuring a biological component according to the values of the average SNRs.

The light source determiner 333 may determine an optimal light source for measuring a biological component based on the calculated SNRs. The optimal light source for measuring a biological component may be changed according to a position at which light is emitted and a position at which a light signal is detected, and the light source determiner 333 may determine an optimal light source based on the calculated SNRs, regardless of change in position at which the biological component is measured.

For example, referring to FIGS. 3 and 4A, the light source determiner 333 may determine a light source at an optimal position for measuring a biological component according to the values of the SNRs calculated by each of the detectors 421 to 426. For example, the light source (e.g., 411) with the highest SNR which is calculated based on the light signals of each of the light sources, which are detected by the detectors 421 to 426, may be determined as the light source at an optimal position for the measurement position.

In another example, the light source determiner 333 may determine a light source of an optimal wavelength for measuring a biological component according to the values of the SNRs calculated by the detectors 421 to 426. For example, when considering a traveling path of the light wavelength, in the case of the back of a hand where the blood vessel is located close to the skin, SNRs of light signals of the green light sources 411 and 412 of a short wavelength may be calculated to be relatively high at each of the detectors (e.g., 421 to 426). In this case, the light source determiner 333 may determine that the green light sources 411 and 412 of a short wavelength, rather than the red light sources 413 and 414 of a long wavelength, are light sources having an optimal wavelength at a corresponding measurement position.

In addition, the light source determiner 333 may calculate an average of SNRs of light signals detected by each of the detectors and determine an optimal light source according to the values of the calculated average. For example, in the case of the wrist where the blood vessel is located further away from the skin, SNRs of light signals of the red light sources 413 and 414 of a long wavelength may be calculated to be relatively high at each of the detectors 421 to 426. In this case, the light source determiner 333 may classify the light signals detected by the detectors (e.g., 421 to 426) into green light and red light, and compare an average SNR of green light with an average SNR of red light so as to determine that the red light source 413 or 414 having the higher average SNR is an optimal light source. Although for convenience of description, FIG. 4A illustrates the case in which green light and red light are emitted to the target object, a wavelength of the light source may be varied (e.g., 400 nm to 1300 nm) to be emitted to the target object, and the light source determiner 333 may determine an optimal wavelength band at a position at which a biological component is measured according to the values of SNRs of light signals detected by one or more detectors 320.

In addition, the light source determiner 333 may simultaneously determine the position and an optimal wavelength band of an optimal light source for measuring a biological component, thereby determining the optimal light source in the multi-light source including one or more light sources which emit light of the same wavelength band.

In another example, the light source determiner 333 may determine the optimal light source based on an SNR of a light signal detected by the optimal detector determined by the detector determiner 332. For example, when the detector determiner 332 selects the detectors 421 and 422 as the optimal detectors, the light source determiner 333 may determine the optimal light source based on SNRs of light signals detected by the detectors 421 and 422. However, embodiments are not limited to the above description, and as described above, the detector determiner 332 may use a light signal of the optimal light source which is determined according to the values of SNRs, calculate an SNR of the light signal for each of the detectors and determine the optimal detectors according to the values of SNRs calculated.

FIG. 4B is a diagram for describing an example of arrangement of the multi-light source 310 and the detector 320. Referring to FIGS. 3 and 4B, the multi-light source 310 may include one or more light sources, and be configured in a predetermined array. FIG. 4B illustrates an example in which the light sources included in the multi-light source 310 have different wavelengths (e.g., red (R), blue (B), green (G), and infrared (I)), but are not limited thereto, and the multi-light source 310 may include multiple light sources having the same wavelength (e.g., light sources R). In this case, the light source determiner 333 may determine that a light source at an optimal position for the location at which a biological component is measured is the optimal light source.

Referring to FIG. 4B, the detector 320 may include one or more detectors (P) that may be disposed in a predetermined array, spaced apart from the multi-light source 310 at a specific distance. The detectors of the detector 320 may be configured in one or more predetermined arrays including a rectangular array and a radial array. However, the predetermined array is not particularly limited.

The component measurer 334 may control the determined optimal light source and the determined optimal detector upon request for measuring a biological component. For example, upon request for measuring a biological component, the component measurer 334 may control the determined optimal light source and the determined optimal detector and measure the biological component based on a light signal of the optimal light source detected by the optimal detector. In one example, the component measurer 334 may calculate a scattered coefficient based on a backscattered light intensity of the light signal detected by the determined detector and measure the biological component using the calculated scattered coefficient. In this case, the component measurer 334 may use one determined optimal light source and two determined optimal detectors and measure the biological component using intensities of light signals detected by the two optimal detectors.

For example, in a case where the component measurer 334 measures the concentration of neutral fat in the blood using Equation 1, the component measurer 334 may compute an amount of change in a reduced scattering coefficient which is defined as a ratio of backscattered intensities detected at the two determined detectors (e.g., a first detector and a second detector) and may measure the concentration of neutral fat of the target object. For example, the component measurer 334 may set one of light signals detected by the optimal detector which is determined in a reference state (e.g., fasting state) in which a biological component of the target object does not change as $R_1$ (e.g., a backscattered intensity at the first detector), set the other as $R_2$ (e.g., a backscattered intensity at the second detector), and calculate the reduced scattering coefficient from Equation 1. In addition, the component measurer 334 may calculate a reduced scattering coefficient after a predetermined amount of time has elapsed since consumption of food containing fat, and compute an amount of change in the reduced scattering coefficient, thereby calculating the concentration of neutral fat.

Figure 5:
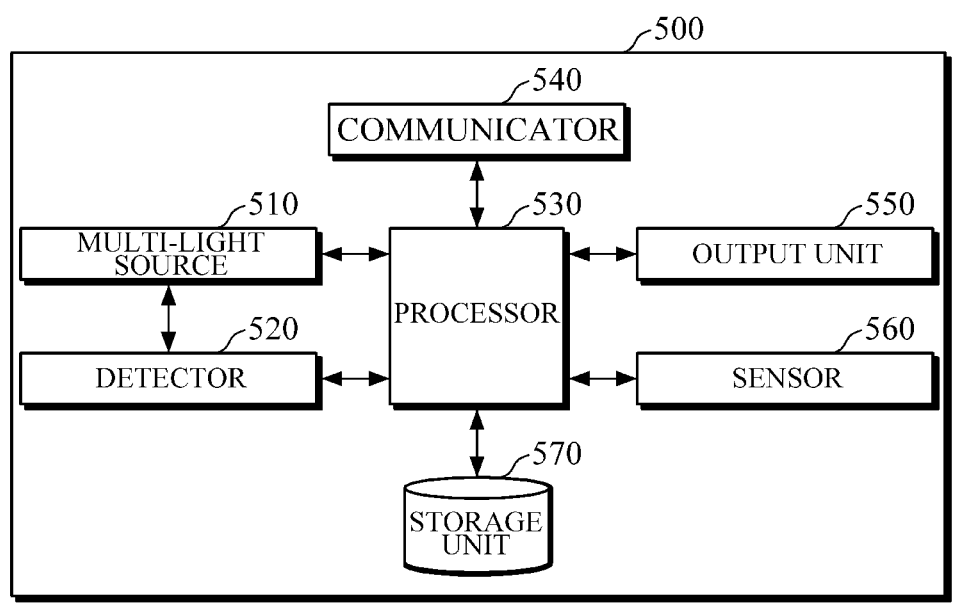
FIG. 5 is a block diagram illustrating an apparatus for measuring a biological component according to another exemplary embodiment.

FIG. 5 is a block diagram illustrating an apparatus for measuring a biological component according to another exemplary embodiment. Referring to FIG. 5, the apparatus 500 for measuring a biological component includes a multi-light source 510, a detector 520, a processor 530, a communicator 540, an output unit 550, a sensor 560, and a storage unit 570. In this case, the multi-light source 510, the detector 520, and the processor 530 may be configured to be basically the same as the multi-light sources 110 and 310, the detectors 120 and 320 and the processors 130 and 330 which are included in the apparatus 100 and 300 for measuring a biological component described with reference to FIGS. 1 and 3, and hereinafter, a description will be given focusing on a configuration which is not redundant.

The communicator 540 may be connected with an external device over a wired/wireless network and transmit a result of biological component measurement to the external device in response to a control signal from the processor 530. For example, the communicator 540 may include one or more modules for communicating via Bluetooth communication. Bluetooth low energy (BLE) communication, near-field communication (NFC), wireless local area network (WLAN) communication, ZigBee communication, infrared data association (IrDA) communication, Wi-Fi direct (WFD) communication, ultra-wideband (UWB) communication. Ant+ communication, Wi-Fi communication, radio frequency identification (RFID) communication, 3G communication, 4G communication, 5G communication, or the like. In this case, the external device may include a smartphone, a tablet personal computer (PC), a mobile terminal, such as a mobile communication terminal, a desktop PC, a notebook PC, a laptop PC, and the like.

The processor 530 may not detect a light signal from the multi-light source 510 and the detector 520 of the apparatus 500, but instead acquire information about the light signal from the external device through the communicator 540. In this case, the processor 530 may control the communicator 540 and receive the information about the light signal of the target object from an external apparatus for detecting a light signal.

The output unit 550 may output various information including an output state (e.g., a flashing state, a wavelength band, etc.) of the multi-light source 510, an arrangement state (e.g., an array structure, etc.) of the detector 520, an SNR of the light signal detected by the detector 520, an optimal light source and optimal detector determination result of the processor 530, a biological component measurement result, and a data transmission/reception state of the communicator 550.

For example, the output unit 550 may be a touchscreen display which displays the optimal light source and optimal detector determination result of the processor 530 and the biological component measurement result in different sections and includes a user interface (UI) that displays a biological component to be detected and detailed information of the user. However, the output unit 550 is not limited to the above example, and may output the information using a non-visual output method, such as an audible method (e.g., voice alarm, etc.) or a tactile method (e.g., vibration, etc.).

The sensor 560 may sense whether the measurement position of the target object is changed. For example, when the apparatus 500 is mounted in a mobile terminal or a wearable device, a position to which the multi-light source 510 emits light and/or a position at which the detector 520 detects a light signal for measuring a biological component may vary according to movement of a user or a change of user. In this case, the sensor 560 may sense the change in measurement position of the target object when the position of the multi-light source 510 and/or the position of the detector 520 deviate from a predetermined threshold range.

For example, the apparatus 500 is mounted in a wearable device (e.g., a smart watch) worn on a wrist, the sensor 560 senses an initial position and determine that the measurement position of the target object has changed when a change in position outside a radius of 1 cm from the center of the initial position is detected. In this case, the sensor 560 may include at least one of an acceleration sensor, a gyro sensor, a motion sensor, a displacement sensor, a pressure sensor, a proximity sensor, a gravity sensor, and an image sensor, but embodiments are not limited thereto.

When the sensor 560 detects a change in measurement position of the target object, the processor 530 may re-detect the optimal light source and/or the optimal detector. That is, the apparatus 500 may detect a biological component of the target object by determining the optimal light source and/or the optimal detector in the process of initialization, and update the optimal light source and/or the optimal detector when the measurement position of the target object has been changed.

The storage unit 570 may store various information including an output state (e.g., a flashing state, a wavelength band, etc.) of the multi-light source 510, an arrangement state (e.g., an array, etc.) of the detector 520, an SNR of the light signal detected by the detector 520, an optimal light source and optimal detector determination result of the processor 530, a biological component measurement result, and a data transmission/reception state of the communicator 550. For example, the storage unit 570 may store the measurement result by categorizing the biological components of the target object, and when the optimal light source and/or the optimal detector are re-determined according to a change in measurement position of the target object, the storage unit 570 may store the measurement result by classifying optimal light source and/or the optimal detector at the changed measurement position.

In this case, the storage unit 570 may include a flash memory, a hard disk, a micro type multimedia card, and a card type memory (e.g., SD or XD memory), a random access memory (RAM), a static random access memory (SRAM), a read only memory (ROM), an electrically erasable programmable read only memory (EEPROM), a programmable read only memory (PROM), a magnetic memory, a magnetic disk, and an optical disk, but embodiments are not limited thereto.

Figure 6:
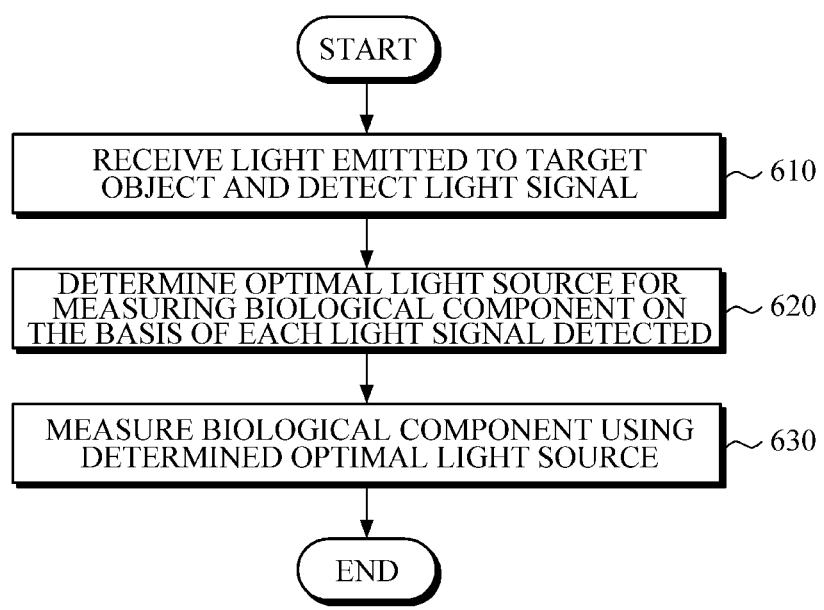
FIG. 6 is a flowchart illustrating a method of measuring a biological component according to an exemplary embodiment.

FIG. 6 is a flowchart illustrating a method of measuring a biological component according to an exemplary embodiment. The method shown in FIG. 6 may one example of a method performed by the apparatus 100 of FIG. 1 to measure a biological component.

Referring to FIGS. 1 and 6, the apparatus 100 emits light to the target object using the multi-light source, as depicted in 610. For example, the apparatus 100 may include one or more light sources which emit light of a wavelength band from 400 nm to 1300 nm (e.g., a specific visible wavelength band, an NIR band, or an MIR band). In this case, the multi-light source may include one or more light sources consisting of independent modules, and the one or more light sources may be disposed at different positions when the light sources are set to emit light of the same wavelength band. For example, the apparatus 100 may sequentially emit light of the same wavelength using the one or more light sources. However, embodiments are not limited thereto, and apparatus 100 may simultaneously emit light of different wavelength bands to the skin of the user using one or more light sources.

Thereafter, the apparatus 100 receives the light emitted to the target object and detects a light signal, as depicted in 610. For example, the apparatus 100 may detect the light signal from light reflected from the skin of the target object which is irradiated by the multi-light source, absorption light, and/or light scattered by a biological component. In addition, the apparatus 100 may include one or more detectors, and the detectors may be implemented as an array of a predetermined structure spaced apart from the multi-light source 110 at a specific distance. Hereinafter, the light signal which will be described as needed may refer to a signal obtained by one or more detectors which detect light scattered by a biological component which is irradiated by the multi-light source 110.

The apparatus 100 determines an optimal light source for measuring a biological component based on each light signal detected, as depicted in 620. For example, the optimal light source for measuring a biological component may vary depending on the position of the multi-light source and/or the detector, and the optimal light source may refer to a light source at a specific location among one or more light sources included in the multi-light source. However, aspects of the present disclosure are not limited to the above description, and when the multi-light source includes one or more light sources, each of which is set to emit light of a specific wavelength band, the optimal light source may refer to a light source which emits light of a particular wavelength band.

For example, referring to FIGS. 6 and 2A, the apparatus 100 may include the multi-light source 210 including a blue light source 211 (e.g., a wavelength band of 450 nm), a green light source 212 (e.g., a wavelength band of 550 nm), a red light source 213 (e.g., a wavelength band of 700 nm), and an infrared light source 214 (e.g., a wavelength band of 1100 nm). In this case, light of a longer wavelength penetrates the skin deeper, and when considering the optical path according to a wavelength, light signals caused by scattering which are detected by one or more detectors 220 may be measured differently for each detector 220 according to a distance between the skin and the blood vessel (e.g., a depth of the blood vessel). In one example, the apparatus 100 may calculate an SNR of each of the light signals detected by one or more detectors 220 and select a light source which emits light of a wavelength band with the highest SNR as the optimal light source. As such, the apparatus 100 uses the multi-light source 210 and one or more detectors 220 so that even when the depth of the blood vessel 231 varies according to the measurement position of the target object, it is possible to accurately measure a biological component by determining the optimal light source and/or the optimal detector in consideration of the distance from the skin to the blood vessel.

The apparatus 100 may measure a biological component using the determined optimal light source. In this case, the biological component may include at least one of neural fat, cholesterol, proteins, blood sugar, and uric acid, but is not limited thereto. For convenience of description, hereinafter, the description will focus on an exemplary embodiment in which the apparatus measures the concentration of neutral fat.

For example, the apparatus 100 may measure the concentration of neutral fat using Equation 1 to calculate a backscattered intensity detected from the light of the determined optimal light source. For example, the apparatus 100 may calculate a reduced scattering coefficient in a reference state (e.g., fasting state) in which a biological component of the target object does not change, calculate a reduced scattering coefficient after a predetermined amount of time has elapsed since consumption of food containing fat, and compute an amount of change in the reduced scattering coefficient, thereby calculating the concentration of neutral fat.

Figure 7:
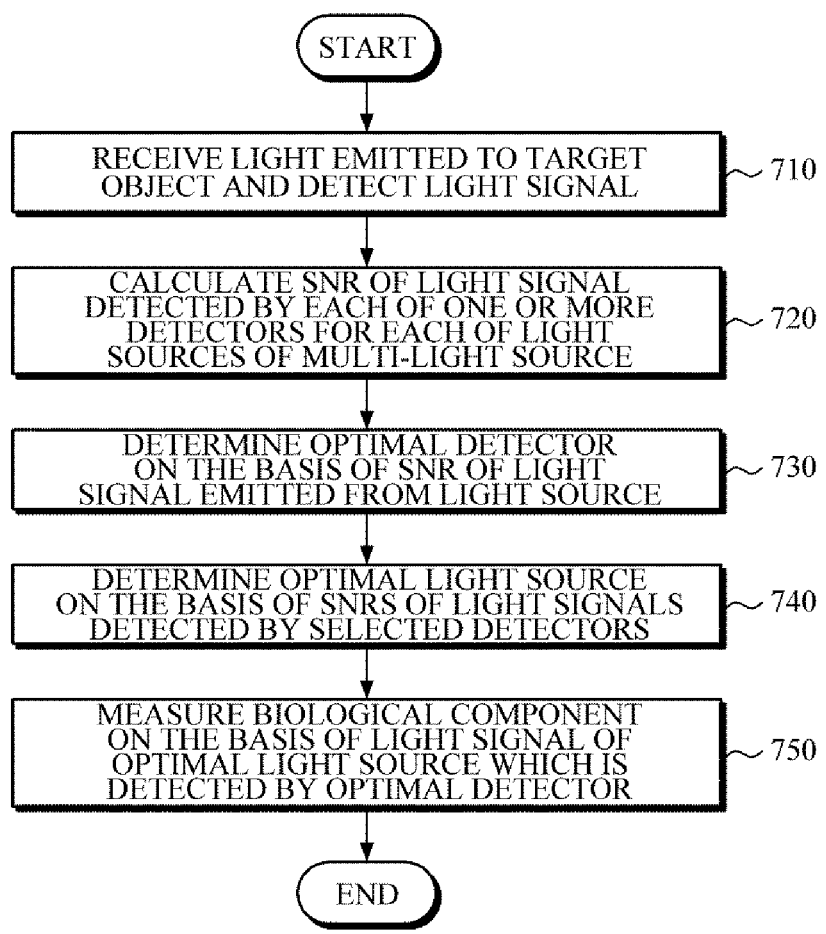
FIG. 7 is a flowchart illustrating a method of measuring a biological component according to another exemplary embodiment.

FIG. 7 is a flowchart illustrating a method of measuring a biological component according to another exemplary embodiment. The method shown in FIG. 7 may be one example of a method performed by the apparatus 300 shown in FIG. 3 to measure a biological component.

Referring to FIGS. 3 and 7, the apparatus 300 receives the light emitted to the target object and detects a light signal, as depicted in 710.

The apparatus 300 calculates an SNR of the detected light signal, as depicted in 720. For example, the apparatus 300 may include a multi-light source and one or more detectors, and calculate an SNR of each light signal detected by each of the detectors for each of light sources included in the multi-light source, as depicted in 720.

For example, the apparatus 300 may calculate an SNR for each light source using the light signal detected by one detector, calculate an SNR for each light source using the light signal detected by another detector, and in this manner, may calculate SNRs of the light signals detected by the detectors for each of the light sources.

The apparatus 300 determines an optimal detector for measuring a biological component based on the SNRs of light signals emitted from the light sources, as depicted in 730. The optimal light source for measuring a biological component may vary according to a position at which light is emitted and/or a position at which a light signal is detected, and the apparatus 300 may determine the optimal light source based on the calculated SNRs, regardless of change in position at which the biological component is measured. For example, the apparatus 300 may determine the optimal detector for measuring a biological component according to the values of the SNRs calculated by the detectors. For example, when considering a traveling path of the light wavelength, in the case of the back of a hand where the blood vessel is located close to the skin. SNRs of light signals detected by detectors located close to the multi-light source may be calculated to be high. In this case, the apparatus 300 may select the detector having the highest SNR as the optimal detector.

In another example, the apparatus 300 may calculate an SNR of a light signal detected from the light emitted from each of the light sources of the multi-light source, sum up the SNRs at each of the detectors, and calculate an average of the SNRs at each of the detectors, thereby selecting at least some detectors as optimal detectors for measuring a biological component according to the values of the average SNRs.

When the optimal detector is determined, the apparatus 300 determine an optimal light source based on SNRs of light signals detected by the determined optimal detectors, as depicted in 740. The optimal light source for measuring a biological component may vary according to a position at which light is emitted and/or a position at which a light signal is detected, and the apparatus 300 may determine the optimal light source based on the calculated SNR, regardless of change in position at which the biological component is measured.

For example, the apparatus 300 may determine the light source at an optimal position for measuring a biological component according to the values of the SNRs calculated by each of the detectors. For example, the light source with the highest SNR which is calculated based on the light signals of each of the light sources, which are detected by the detectors, may be determined as the light source at an optimal position for the measurement position.

In another example, the apparatus 300 may determine the light source of an optimal wavelength for measuring a biological component according to the values of the SNRs calculated by each of the detectors. For example, when considering a traveling path of the light wavelength, in the case of the back of a hand where the blood vessel is located close to the skin, an SNR of light signal of a green light source of a short wavelength may be calculated to be generally high at each of the detectors. In this case, the apparatus 300 may determine that the green light source of a short wavelength, rather than a red light source of a long wavelength, is a light source having an optimal wavelength at a corresponding measurement position. However, the method of determining the optimal light source among the light sources included in the multi-light source is not limited to the above description, and the apparatus 300 may calculate an average of the SNRs of the light signals detected by each of the detectors, and determine the optimal light source according to the value of the calculated average. In one example, the apparatus 300 may compare an average SNR of green light with an average SNR of red light and select a red light source with a higher average SNR as the optimal light source.

Upon request for measuring a biological component, the apparatus 300 controls the determined optimal light source and optimal detector and measures a biological component based on a light signal of the optimal light source detected by the optimal detector, as depicted in 750. For example, the apparatus 300 may calculate a scattered coefficient based on a backscattered light intensity of the light signal detected by the determined detector and measure the biological component using the calculated scattered coefficient. In this case, the apparatus 300 may use one determined optimal light source and two determined optimal detectors and measure the biological component using intensities of light signals detected by the two optimal detectors.

Figure 8:
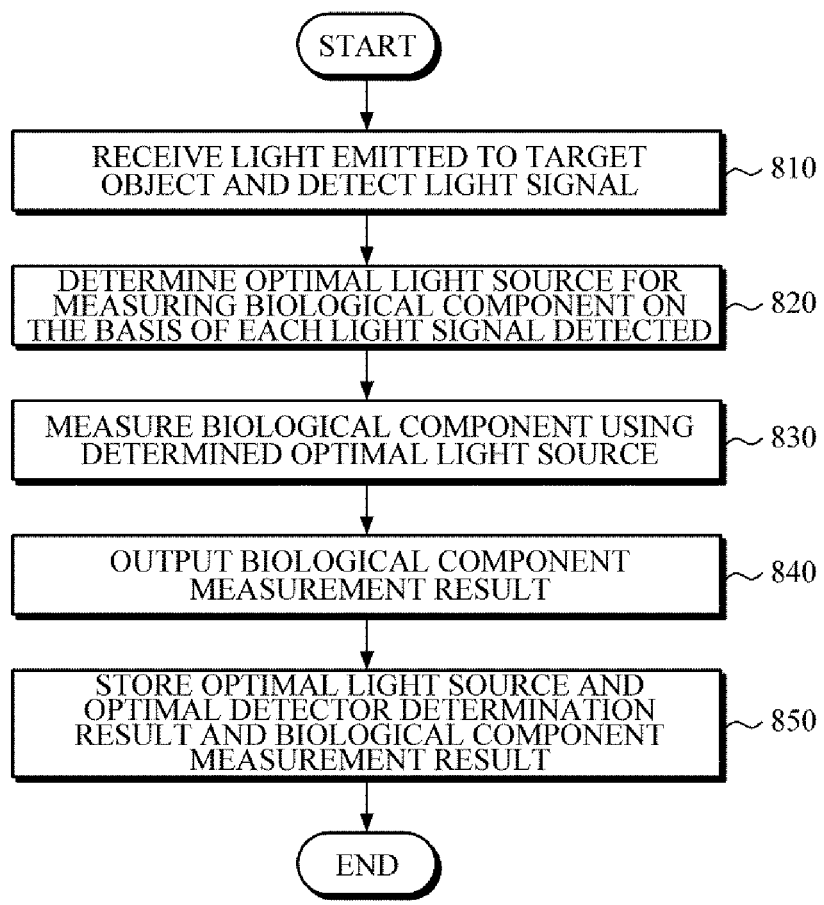
FIG. 8 is a flowchart illustrating a method of measuring a biological component according to still another exemplary embodiment.

FIG. 8 is a flowchart illustrating a method of measuring a biological component according to still another exemplary embodiment. The method shown in FIG. 8 may be one example of a method performed by the apparatus 500 shown in FIG. 5 to measure a biological component.

Referring to FIGS. 5 and 8, the apparatus 500 detects receives the light emitted to the target object and detects a light signal, as depicted in 810.

The apparatus 500 determines an optimal light source for measuring a biological component based on each of the detected light signals, as depicted in 820. For example, the apparatus 500 may calculate an average of SNRs of light signals detected by each of the detectors and determine the optimal light source according to the value of the calculated average.

When the optimal light source is determined, the apparatus 500 measures a biological component using the determined optimal light source, as depicted in 830. For example, the apparatus 500 may use at least two detectors to receive the light emitted from the determined optimal light source and detect light signals from the light, calculate a scattered coefficient based on backscattered light intensities of the detected light signals, and measure the biological component based on the calculated scattered coefficient. In this case, the apparatus 500 may use one determined optimal light source and two determined optimal detectors to measure the biological component using the intensities of the light signals detected by the two detectors.

The apparatus 500 outputs various information including the biological component measurement result, as depicted in 840. For example, the apparatus 500 may output the information including an output state (e.g., a flashing state, a wavelength band, etc.) of the multi-light source, an arrangement state (e.g., an array structure, etc.) of the detector, an SNR of the light signal detected by the detector, an optimal light source and optimal detector determination result, a biological component measurement result, and a data transmission/reception state. In this case, the apparatus 500 may output the information using visual and/or non-visual output methods.

In addition, the apparatus 500 may store the various information including the optimal light source and optimal detector determination result and the biological component measurement result, as depicted in 850. For example, the apparatus 500 may store the measurement result by categorizing the biological components of the target object, and when the optimal light source and/or the optimal detector are re-determined according to a change in measurement position of the target object, the apparatus 500 may store the measurement result by classifying optimal light source and/or the optimal detector at the changed measurement position.

The apparatus 500 may sense whether the measurement position of the target object is changed. For example, when the apparatus 500 is mounted in a mobile terminal or a wearable device, a position to which the multi-light source emits light and/or a position at which the detector detects a light signal for measuring a biological component may vary according to movement or the change of user. In this case, when the apparatus 500 detects a change in measurement position of the target object, the apparatus 500 may re-detect the optimal light source and/or the optimal detector. That is, the apparatus 500 may detect a biological component of the target object by determining the optimal light source and/or the optimal detector in the process of initialization, and update the optimal light source and/or the optimal detector when the measurement position of the target object has been changed.

As described above, by updating the optimal light source and/or the optimal detector, it is possible to perform biological component measurement immediately upon request.

The exemplary embodiments can be implemented as computer readable codes or programs stored in a computer readable recording medium. Codes and code segments constituting the computer program can be inferred by a skilled computer programmer in the art. The computer readable recording medium includes all types of non-transitory recording media in which computer readable data are stored. Examples of the computer readable recording medium include a ROM, a RAM, a CD-ROM, a magnetic tape, a floppy disk, and an optical data storage. In addition, the computer readable record medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for measuring a biological component, the apparatus comprising:
   light sources configured to emit light that irradiates a target object;
   detectors configured to receive light from the target object that is irradiated by the light emitted by the light sources and to detect light signals corresponding to the light received from the target object; and
   a processor configured to determine an optimal light source, from among the light sources, based on the light signals detected by the detectors and to measure a biological component of the target object using the optimal light source,
   wherein the processor comprises a detector determiner configured to determine two optimal detectors for measuring the biological component, from among the detectors, based on signal-to-noise ratios of light signals detected by the detectors, and
   wherein the processor further comprises a component measurer configured to determine a scattered coefficient based on backscattered light intensities of light signals detected by the two optimal detectors and to measure the biological component of the target object based on the scattered coefficient.

2. The apparatus of claim 1, wherein the processor comprises a signal-to-noise ratio determiner configured to determine the signal-to-noise ratios of light signals detected by the detectors.

3. The apparatus of claim 2, wherein the processor further comprises a light source determiner configured to select at least one detector, from among the detectors, based on the signal-to-noise ratios and to determine the optimal light source based on the signal-to-noise ratios of light signals detected by the at least one detector that is selected.

4. The apparatus of claim 3, wherein the processor is further configured to determine an average of signal-to-noise ratios of the light signals detected by the at least one detector and determine the optimal light source based on the average.

5. The apparatus of claim 1, wherein the component measurer is further configured to control the optimal light source and the two optimal detectors and to measure the biological component on a light signal corresponding to the optimal light source which is detected by the two optimal detectors.

6. The apparatus of claim 1, wherein the light sources are further configured to emit light of different wavelength bands and the detectors are arranged in one of a rectangular array and a radial array.

7. The apparatus of claim 1, wherein the biological component comprises at least one of neural fat, cholesterol, proteins, blood sugar, and uric acid.

8. The apparatus of claim 1, further comprising:
   a communicator configured to be communicably connected with an external device and to transmit a biological component measurement result to the external device in response to a control signal from the processor; and
   an output unit configured to output the biological component measurement result.

9. The apparatus of claim 1, further comprising:
   a sensor configured to sense whether a measurement position of the target object is changed,
   wherein the processor is further configured to repeat determination of the optimal light source in response to the sensor detecting that the measurement position of the target object is changed.

10. A method of measuring a biological component, the method comprising:
    receiving, at detectors, light from a target object that is irradiated with light by light sources;
    detecting, at the detectors, light signals corresponding to the light from the target object;
    determining an optimal light source of the target object, from among the light sources, based on the light signals detected by the detectors; and
    measuring a biological component of the target object using the optimal light source,
    the method further comprising:
       determining two optimal detectors for measuring the biological component, from among the detectors, based on signal-to-noise ratios of light signals detected by the detectors, and
       determining a scattered coefficient based on backscattered light intensities of light signals detected by the two optimal detectors and measuring the biological component of the target object based on the scattered coefficient.

11. The method of claim 10, further comprising determining signal-to-noise ratios of the light signals detected by the detectors.

12. The method of claim 11, wherein the determining the optimal light source comprises selecting at least one detector among the detectors based on the signal-to-noise ratios, and determining the optimal light source based on the signal-to-noise ratios of the light signals detected by the at least one detector that is selected.

13. The method of claim 12, wherein the determining the optimal light source comprises determining an average of signal-to-noise ratios of the light signals detected by the at least one detector that is selected, and determining the optimal light source based on the average.

14. The method of claim 10, wherein the measuring the biological component comprises controlling the optimal light source and the two optimal detectors, and measuring the biological component based on a light signal corresponding to the optimal light source which is detected by the two optimal detectors.

* * * * *